United States Patent [19]

Guzzi et al.

[11] Patent Number: 5,618,822
[45] Date of Patent: Apr. 8, 1997

[54] N-SUBSTITUTED TRIFLUOROMETHYLPHENYLTETRA-HYDROPYRIDINES, PROCESS FOR THE PREPARATION THEREOF, INTERMEDIATES IN SAID PROCESS AND PHARMACEUTICAL COMPOSITIONS CONTAINING THEM

[75] Inventors: Umberto Guzzi; Costantino Palmieri; Tiziano Croci, all of Milan, Italy

[73] Assignee: Sanofi, France

[21] Appl. No.: 477,569

[22] Filed: Jun. 7, 1995

Related U.S. Application Data

[63] Continuation-in-part of Ser. No. 141,066, Oct. 26, 1993, Pat. No. 5,462,945, which is a continuation of Ser. No. 705,704, May 23, 1991, Pat. No. 5,281,606.

[30] Foreign Application Priority Data

May 23, 1990 [FR] France .................................. 90 06474

[51] Int. Cl.⁶ .................................................. A61K 31/44
[52] U.S. Cl. ............................................................. 514/277
[58] Field of Search ............................. 514/277; 546/339

[56] References Cited

U.S. PATENT DOCUMENTS

| | | | |
|---|---|---|---|
| 4,213,989 | 7/1980 | Nedelec et al. ...................... | 514/277 |
| 4,521,428 | 6/1985 | Nisato et al. . | |
| 5,026,716 | 6/1991 | Bianchetti et al. . | |
| 5,109,005 | 4/1992 | Croci et al. ...................... | 514/277 |
| 5,229,389 | 6/1993 | Coude et al. . | |
| 5,266,573 | 11/1993 | Croci et al. . | |
| 5,270,320 | 12/1993 | Coude et al. ...................... | 514/277 |
| 5,468,753 | 11/1995 | Coude et al. ...................... | 514/277 |

FOREIGN PATENT DOCUMENTS

| | | |
|---|---|---|
| 0101381 | 2/1984 | European Pat. Off. . |
| 881894 | 11/1961 | United Kingdom . |
| 2083476 | 3/1982 | United Kingdom . |

OTHER PUBLICATIONS

Bottenstein, J.E. "Growth and Differentation of Neural Cells in Defined Media", Cell Culture in the Neuroscience, 3–43, 1985.

Muller, H.W., Seifert, W. "A Neurotrophic Factor (NTF) Released From Primary Glial Cultures Supports Survival and Fiber Outgrowth of Cultured Hippocampal Neurons", J. Neurosci. Res., 8(2/3), 195–204, 1982.

Fournier, J., Steinberg, R., Gauthier, T., Keane, P.E., Guzzi, U., Coude, F.X., Bougault, I., Maffrand, J.P., Soubrie, P., LeFur, G. "Protective Effects of SR 57746A in Central and Peripheral Models of Neurodegenerative Disorders in Rodents and Primates", 1993.

*Primary Examiner*—C. Warren Ivy
*Assistant Examiner*—Lyman H. Smith
*Attorney, Agent, or Firm*—Bacon & Thomas

[57] ABSTRACT

A method is disclosed for the treatment of neuronal degenerative processes. The method comprises administering 1-[4-(3-trifluoromethylphenyl)-1, 2, 3, 6-tetrahydropyrid-1-yl]-2-)6, 7-dimethoxynaphth-2-yl)ethane or a pharmaceutically acceptable salt thereof to a mammal suffering from a neuronal degenerative process.

3 Claims, No Drawings

N-SUBSTITUTED TRIFLUOROMETHYLPHENYLTETRA-HYDROPYRIDINES, PROCESS FOR THE PREPARATION THEREOF, INTERMEDIATES IN SAID PROCESS AND PHARMACEUTICAL COMPOSITIONS CONTAINING THEM

This application is a continuation-in-part of application Ser. No. 08/141,066, filed Oct. 26, 1993, now U.S. Pat. No. 5,462,945, issued Oct. 31, 1995, which is a continuation of application Ser. No. 07/705,704, filed May 23, 1991, now U.S. Pat. No. 5,281,606, issued Jan. 25, 1991.

The present invention concerns new N-substituted 4-(3-trifluoromethylphenyl)-1,2,3,6-tetrahydropyridines useful in the treatment of intestinal motility disorders.

More particularly, the present invention refers to new compounds of the following general formula

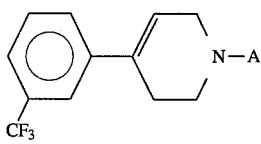 (I)

wherein
A represents a group —E—G or —L—M, where
—E— is a straight or branched alkylene radical of from 2 to 4 carbon atoms,
—G represents a radical selected from the group consisting of naphthyl mono-substituted with hydroxy or $(C_1-C_4)$alkoxy: naphthyl di-substituted with hydroxy, $(C_1-C_4)$alkoxy or $(C_1-C_4)$alkyl; or naphthyl substituted with methylenedioxy,
—L— is a —Q—CH(OH)— group wherein —Q— is a straight or branched alkylene radical of from 1 to 3 carbon atoms, and
—M represents a radical selected from the group consisting of naphthyl; naphthyl mono- or di-substituted with hydroxy, $(C_1-C_4)$alkoxy or $(C_1-C_4)$alkyl or naphthyl substituted with methylenedioxy; pyridyl; or $(C_1-C_4)$alkyl-pyridyl,
and their salts with mineral or organic acids.

GB-A-881894 describes 1-aroylalkyl-4-aryl-1,2,3,6-tetrahydropyridines of formula

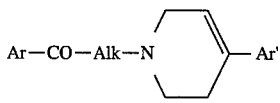

wherein Ar and Ar' represent a halophenyl, alkoxyphenyl, dimethoxyphenyl, hydroxyphenyl, thienyl, trifluoromethylphenyl, or alkylphenyl group, and Alk represents an alkylene chain of from 3 to 6 carbon atoms, with anticonvulsant, CNS depressant and tranquillizing activity.

Belgian patent BE-837878 describes, as intermediates, some tetrahydropyridines of formula

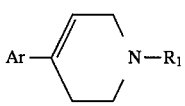

wherein Ar is an aryl group optionally substituted with one or more groups selected from alkyl, alkoxy, halogen, and $CF_3$, and $R_1$ may represent, inter alia, a group

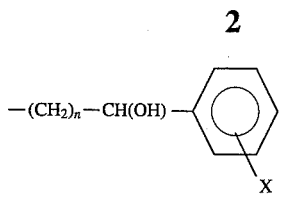

wherein n is 1, 2, 3, or 4 and X may represent hydrogen or halogen. French patent FR-1421208 claims tetrahydropyridine derivatives of formula

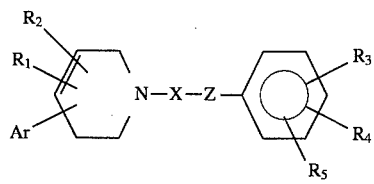

wherein, inter alia, Ar may represent a phenyl radical optionally substituted with trifluoromethyl; $R_1$ and $R_2$ may represent, inter alia, a bond; X is an alkylene or an alkenylene of 2 or 3 carbon atoms; 2 represents a single bond or a group —$CH_2$—, —CH(OH)—, —CO—, or —CH(alkyl)— and $R_3$ is a m- or p-substituent while $R_4$ and $R_5$ may represent hydrogen atoms or substituents.

These compounds are described as psychotropes, hypothermic, antiemetic, and general anesthetic potentiating agents.

German patent application DE-A-2904826 describes tetrahydropyridines of formula

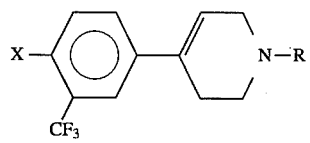

wherein X is a hydrogen or a chlorine atom and R is hydrogen, alkyl, alkenyl, alkynyl, or phenyl-alkyl, which are endowed with anorexigenic activity and may also be employed in the treatment of depression.

European patent application EP-A-0060176 claims 4-(3-trifluoromethylphenyl)-1,2,3,6-tetrahydropyridines of formula

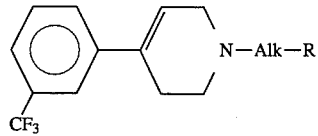

wherein R represents a cyano, acetyl, or cycloalkyl group of from 3 to 7 carbon atoms, and Alk represents a straight or branched alkylene of from 1 to 4 carbon atoms, as well as their salts, endowed with anorexigenic activity.

4-Aryl-1,2,3,6 tetrahydropyridine derivatives of formula

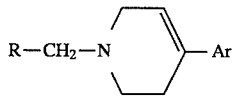

wherein Ar may be a phenyl group substituted i.a. with a —$CF_3$ group and R may represent naphthyl have been described in British patent GB-2083476 as psychotropes.

Anorexigenic trifluoromethylphenyltetrahydropyridine derivatives of formula

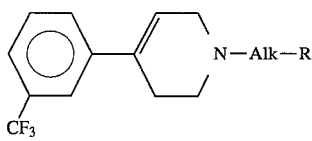

wherein R represents pyridyl, pyridyl-3-oxide, or naphthyl, unsubstituted or substituted with a $(C_1-C_4)$alkyl group and Alk represents a straight or branched alkylene chain of from 2 to 4 carbon atoms have been described in European patent application EP-A-0101381. Finally, WO-A-8905779 describes N-alkenyl- or N-alkynyl-tetrahydropyridines of formula

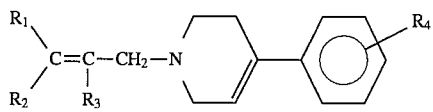

wherein $R_1$, $R_2$, and $R_3$ may be hydrogen atoms or alkyl groups, or $R_2$ and $R_3$ taken together may represent an additional bond and $R_4$ is a halogen atom, a $—CF_3$ or an alkyl group, which show gastro-intestinal mucous membrane protecting activity and may therefore be employed for treating or preventing gastric ulcers.

It has now been found that the N-substituted trifluoromethylphenyltetrahydropyridines (I) of the present invention increase intestinal motility in mammals thus exerting an anti-constipation effect. Some of them have also been tested as antidepressant agents, showing a good antidepressive activity. For the scope of the present invention, the terms "$(C_1-C_4)$alkyl" and "$(C_1-C_4)$alkoxy" include straight or branched alkyl or alkoxy radicals containing of from 1 to 4 carbon atoms such as methyl, ethyl, propyl, isopropyl, butyl, and methoxy, ethoxy, propoxy, isopropoxy, and butoxy, methyl and methoxy being preferred. "Substituted naphthyl" may represent a 1-naphthyl or 2-naphthyl radical bearing one or two substituents at positions 5-, 6-, 7-, and/or 8-.

Salts of the compounds of formula (I) according to the present invention comprise both the pharmaceutically acceptable addition salts with mineral or organic acids, such as the hydrochloride, hydrobromide, sulfate, hydrogensulfate, dihydrogenphosphate, citrate, maleate, tartrate, fumarate, gluconate, methansulfonate, 2-naphthalensulfonate, and the like salts, and the acid addition salts with mineral or organic acids which allow an easy separation or crystallisation of the compounds of formula (I), such as the picrate, oxalate, and the like. A preferred group of compounds of the present invention comprises those compounds of formula (I) wherein A is —E—G wherein —E— is —$CH_2$—$CH_2$—, wherein one of the hydrogen atoms may be replaced by a methyl group, and —G represents naphthyl substituted with one or two hydroxy or methoxy groups, or with two methyl groups. Another preferred group of compounds of the present invention comprises those compounds of formula (I) wherein A is —L—M wherein —L— is —Q—CH(OH)— where —Q— stands for —$CH_2$— or —CH($CH_3$)— and —M is as defined above. Particularly preferred compounds of this last group are those compounds wherein —M is naphthyl, naphthyl substituted with one or two hydroxy, methoxy or methyl groups or pyridyl.

A general method for the preparation of the compounds of formula (I) and their salts comprises the reaction in an organic solvent of 4-(3-trifluoromethylphenyl)-1,2,3,6-tetrahydropyridine (II)

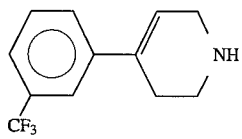

with a compound of formula (III)

X—A (III)

wherein A is as defined above and X represents chloro, bromo, iodo, or a good leaving group such as a methanesulphonate or a p-toluenesulphonate.

As organic solvents, lower alkanols, such as ethanol, n-butanol or n-pentanol, are preferably used, but other solvents such as hexane, dimethylformamide, dimethylsulfoxide, acetonitrile, pyridine, and the like solvents can also be employed.

The reaction is conveniently carried out in the presence of at least an equimolar amount of a basic condensation agent such as an alkali metal carbonate or bicarbonate, e.g. sodium or potassium carbonate, or a tertiary amine, e.g. triethylamino.

The reaction temperature may vary between room temperature and 200° C. The reaction is generally complete in 4 or 5 hours by heating at 80°–150° C., and the thus obtained end product may be isolated according to conventional techniques and optionally converted into one of its addition salts with a suitably selected organic or inorganic acid. Conversion of the free base into an addition salt thereof is easily achieved by treating the free base with the selected acid in an inert organic solvent such as a lower alkanol, e.g. ethanol, or isopropanol, an ether, e.g. dimethoxyethane, or isopropyl ether, an ester, e.g. ethyl acetate, or an aliphatic or aromatic hydrocarbon, e.g. hexane, benzene, or toluene.

When a compound of formula (I) is desired wherein A represents a group —E—G or a group —L—M wherein —G, —L—, and —M are as defined above and —E— is a group —R—$CH_2$— wherein R is a straight or branched alkylene chain of from 1 to 3 carbon atoms, an alternative method is preferably employed which comprises suitably reducing a compound of formula (IV)

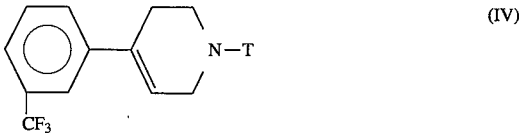

wherein —T represents —R—CO—G or —Q—CO—M wherein —R—, —Q—, —G, and —M are as defined above, and if desired, converting the thus obtained products into the corresponding acid addition salts.

When a compound of formula (I) is desired wherein A represents a group —E—G wherein —E— is a group —R—$CH_2$—, reduction of the carbonyl group to methylene can be carried out according to any of the methods known in the chemical literature, such as for instance, the Clemmensen reduction, which involves treating the carbonyl compound of formula (IV) with excess zinc amalgam in a 20 to 40% hydrochloric acid aqueous solution, optionally in the presence of an organic, water-miecible or immiscible, solvent, at the reflux temperature of the reaction mixture, or treating it with excess zinc amalgam in an organic solvent containing yazeous hydrogen chloride; the Wolff-Kishner or Huang-Minlon reduction, which involves treating the carbonyl compound of formula (IV) with hydrazone or hydrazone hydrate and decomposing the thus obtained hydrazone heating it in a high-boiling glycol to 150°–200° C. in the presence of NaOH or KOH; or even by converting the carbonyl compound of formula (IV) in the corresponding p-toluenesulfonylhydrazone by reaction with p-toluenesulfonylhydrazine, followed by the reduction of the thus obtained product with NaBH$_4$ or, better, NaBH$_3$CN according to the method described by R. O. Hutchins et al. in J.Am.Chem.Soc., 1971, 93, p.1793 et seq.

If on the contrary, a compound of formula (I) is desired wherein A is a group L—M, reduction of the carbonyl group to secondary alcohol may easily be achieved by well known techniques, by means of an aluminum hydride, such as isobutylaluminum hydride (DIBAL), an aluminum lithium hydride, such as LiAlH$_4$, or lithium and trialkoxyaluminum hydrides, boron sodium hydrides, boron zinc hydrides, lithium and trialkylborane hydrides, or analogous hydrides which are suitable to convert a carbonyl compound into a hydroxymethylene group without affecting the other functional groups of the molecule.

The reduction reaction is carried out in an inert organic solvent which is suitably selected depending on the particular reducing agent employed. Particularly, when using DIRAL, preferred organic solvents are benzene, toluene, or 1,2-dimethoxyethane; when using aluminum lithium hydrides, ethers are preferably employed such as ethyl ether, dioxane, tetrahydrofuran, or 1,2-dimethoxyethane; while, when using NaBH$_4$, the reaction is preferably carried out in methanol or ethanol. According to a preferred embodiment of the invention, reduction of the carbonyl group into hydroxymethylene is carried out with a nearly equimolar amount or a slight excess of a reducing agent with respect to the starting substrate of formula (IV), at a temperature comprised between 0° C. and the reflux temperature of the solvent employed and more preferably at room or at a lower temperature under inert atmosphere.

When reduction of the carbonyl compound of formula (IV) is complete, the compound (I) wherein A represents a group —E—G or —L—M is recovered as the free base or its addition salt, —G, —L—, and —M being as defined above and —E— representing a group —R—CH$_2$—.

The compounds of formula (I) wherein A represents a group —E—G wherein —E— is a group —CH$_2$—R—, wherein —R— and —G are as defined above, may also be obtained by reduction of the compounds of formula (V)

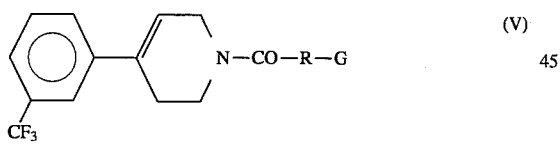

wherein —R— and —G are as defined above, optionally followed by conversion of the thus obtained product into an acid addition salt.

In this case reduction of the amide group may easily be achieved by using an aluminum hydride or a lithium aluminum complex hydride such as LiAlH(OCH$_3$)$_3$ or LiAlH$_4$, in an inert organic solvent such as a linear or cyclic ether e.g. diethyl ether, dioxane, tetrahydrofuran, and 1,2-dimethoxyethane, at a temperature of from 0° C. to the reflux temperature.

According to a preferred embodiment, an equimolar proportion of LiAlH$_4$ with respect to the starting compound of formula (V), is employed and the reaction is carried out at room temperature and under inert atmosphere using tetrahydrofuran or ethyl ether as the reaction solvent.

The reaction is complete in about 1 hour and affords the compound of formula (I) wherein A represents —E—G wherein —E— is a —CH$_2$—R— group, as the free base or an acid addition salt thereof.

The compounds of formula (I) wherein A is the group —L—M wherein —L— is —Q—CH(OH)— wherein —Q— is —CH$_2$— are preferably prepared by reacting the compound of formula (II) with the epoxide (VI)

The condensation reaction between the compound of formula (II) and the epoxide (VI) is typically achieved by heating a mixture of the starting products in a lower alkanol such as ethanol, isopropanol, and butanol, optionally in the presence of a basic condensation agent such as an alkali metal carbonate.

In a preferred embodiment said condensation reaction is carried out by refluxing for a few hours a mixture of the compound (II) with at least the equimolar amount of the epoxide (VI). When the reaction is complete, the end product is isolated by conventional techniques and if desired converted into one of its acid addition salts.

Finally, when by the above processes a compound of formula (I) is obtained wherein A is a group —E—G or —L—M where —G or —M represent naphthyl substituted with one or two methoxy groups, it may be transformed into the corresponding compound wherein —G or —M represent naphthyl substituted with one or two hydroxy groups by demethylation, for instance by treating the methoxylated compound with a concentrated hydrobromic acid solution in water or acetic acid.

Another object of the present invention is therefore a process for the preparation of a compound of formula (I)

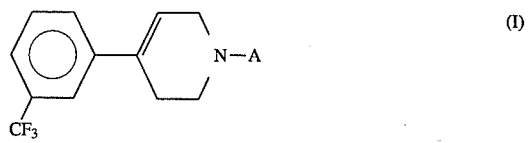

wherein
A represents a group —E—G or —L—M, where
—E— is a straight or branched alkylene radical of from 2 to 4 carbon atoms,
—G represents a radical selected from the group consisting of naphthyl mono-substituted with hydroxy or (C$_1$–C$_4$)alkoxy; naphthyl di-substituted with hydroxy, (C$_1$–C$_4$)alkoxy or (C$_1$–C$_4$)alkyl; or naphthyl substituted with methylenedioxy,
—L— is a —Q—CH(OH)— group wherein —Q— is a straight or branched alkylene radical of from 1 to 3 carbon atoms, and
—M represents a radical selected from the group consisting of naphthyl; naphthyl mono- or di-substituted with hydroxy, (C$_1$–C$_4$)alkoxy or (C$_1$–C$_4$)alkyl or naphthyl substituted with methylenedioxy; pyridyl; or (C$_1$–C$_4$)alkyl-pyridyl,
or of one of its addition salts with mineral or organic acids, which comprises
(a) reacting 4-(3-trifluoromethylphenyl)-1,2,3,6-tetrahydropyridine (II)

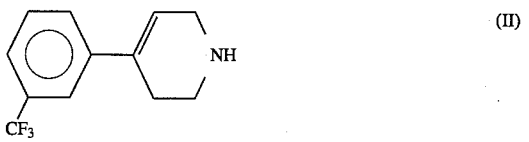

with a compound of formula (III)

wherein A is as defined above and X represents chloro, bromo, iodo, or a good leaving group; such as a methanesulphonate or a p-toluenesulphonate; or (b) when a compound of formula (I) is desired wherein A represents a group —E—G or —L—M wherein —G, —L—, and —M are as defined above and —E— is a group —R—CH$_2$— wherein R is a straight or branched alkylene chain of from 1 to 3 carbon atoms, reducing a compound of formula (IV)

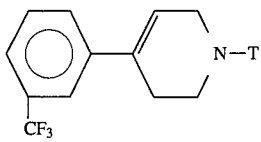 (IV)

wherein —T stands for —R—CO—G or —O—CO—M wherein —R—, —Q—, —G, and —M are as defined above; or (c) when a compound of formula (I) is desired wherein A represents a group —E—G wherein —E— is a group —CH$_2$—R—, wherein —R— and —G are as defined above, reducing the corresponding compound of formula (V)

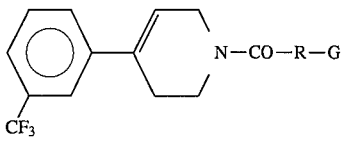 (V)

wherein —R— and —G are as defined above; or (d) when a compound of formula (I) is desired wherein A is the group —L—M wherein L— is —Q—CH(OH)— where —Q— is —CH$_2$— and —M is as defined above reacting 4-(3-trifluoromethylphenyl)-1,2,3,6-tetrahydropyridine (II) with the epoxide (VI)

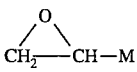 (VI)

wherein —M is as defined above; said process being further characterised in that when a compound of formula (I) is obtained as the free base, it may be converted into an addition salt thereof, when a compound of formula (I) is obtained as addition salt, it may be converted into the corresponding free base or in another addition salt, when a compound of formula (I) is obtained wherein A represents a group —E—G or —L—M wherein —G or —M represent naphthyl substituted with one or two methoxy groups it may be converted into the corresponding compound wherein —G or —M represent naphthyl substituted with one or two hydroxy groups by demethylation.

The starting compounds of formula (III), when not commercially available, may be easily prepared by known methods. In particular, the compounds of formula (III) wherein A represents a group —E—G or —L—M wherein —E— is —R—CH$_2$— and —R—, —G, —L—, and —M are as defined above, may be obtained through Friedel Crafts acylation of compounds H—G or H—M respectively wherein —G and —M are as defined above, with an acid halide of formula (VIIa) or (VIIb) respectively

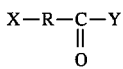 (VIIa)

X—Q—C—Y (VIIb)
‖
O wherein —R— and —Q— are as defined above and Y is a halogen atom such as chloro or bromo, in the presence of a Lewis acid under the conditions which are conventionally employed in this type of reaction (see G.A. Olah, Friedel-Crafts and related reactions, Volumes 1–5, Interscience Publisher, New York, 1963–1967), followed by the reduction of the carbonyl group to methylene or hydroxymethylene.

More particularly, the Friedel-Crafts reaction may be carried out in an inert organic solvent such as carbon sulfide, carbon tetrachloride, methylene chloride, ethylene chloride, nitrobenzene, nitromethane, using AlCl$_3$, FeCl$_3$, SbCl$_5$, SnCl$_4$, ZnCl$_2$, BF$_3$, TiCl$_3$, and the like acids as the Lewis acids, preferably in equimolar amount or in a slight excess over the acylating agent. Generally, the catalyst is added to a mixture of the two reactants or the substrate HC or HM is added to a mixture of the catalyst and the acyl halide (VII). The reaction may well proceed at room temperature but, depending on the substrates and the reactants, as well as on the reaction solvents and catalysts which are employed it may better be carried out either at a lower or higher temperature, typically at a temperature comprised between −15° C. and the reflux temperature of the reaction mixture, preferably between −10° C. and 40° C. When a compound of formula (III) is desired wherein A is a group —E—G or —L—M wherein —G or —M contain one or two hydroxy substituents, either a Friedel-Crafts catalyst is employed which does not react with the hydroxy groups, such as ZnCl$_2$ or BF$_3$, or the acyl halide (VII) is reacted with compounds HG' or HM' which correspond to the compounds HG or HM respectively wherein the hydroxy groups have been protected as the corresponding methyl ethers and, at the end of the reaction, said methyl groups are conveniently removed by treatment of the acylated product with an additional amount of AlCl$_3$ at high temperatures. Depending on the optional substitution of the naphthalene or pyridine moieties and the positions of such optional substituents, the Friedel-Crafts reaction may afford one or more positional isomers of the compounds of formula X—R—CO—G or X—Q—CO—M. If a mixture of isomers is obtained, it may be separated into the single isomers, e.g. by column chromatography, before or after reduction of the carbonyl group. Known techniques may be applied to the reduction step such as those described above.

The compounds of formula (III) wherein A represents a group —E—G wherein —E— stands for —CH$_2$—R— and —R— and —G are as defined above, may be prepared by converting the corresponding acid (VIII)

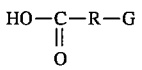 (VIII)

into the lower alkyl esters thereof, typically the ethyl ester, reducing the ester group to a primary alcoholic group by a mixed hydride such as LiAlH$_4$, and replacing the hydroxy group with a group X by a nucleophilic substitution reaction with an acid H—X wherein X attacks the positively polarised alcoholic carbon atom.

In their turns, the acids of formula (VIII) may be prepared, depending on the meaning of —R—, by a number of different methods which are however entirely known to any skilled technician. In particular, as an example, the acids of formula (VIII) wherein —R— is —CH$_2$— may be prepared by heating a mixture of the compound G—H and bromoacetic or chloroacetic acid in the presence of catalytic amounts of KBr, for a few hours and isolating the desired product by chromatography.

Alternatively, and preferably, the acids of formula (VIII) wherein —R— represents —$CH_2$— may be prepared through a three-step process which involves as the first step, Friedel-Crafts acylation of the compound of formula G—H with acetyl chloride or bromide in the presence of catalytic amounts of a Friedel-Crafts catalyst such as for instance $AlCl_3$ or another Lewis acid, followed, in the second step, by conversion of the acetyl group into morpholinylthioacetyl by refluxing for a few hours a mixture of the acetylated product and a slight molecular excess of sulfur in morpholine, and, in the third step, by treatment of the thus obtained product with sodium hydroxide in ethanol at the reflux temperature of the reaction mixture and acid hydrolycic of the thus obtained acid (VIII) sodium salt. The thus obtained products may be converted into the corresponding α-methyl, α-ethyl, α,α-dimethyl derivatives (R=CH($CH_3$)—, —CH($CH_2CH_3$)—, or —C($CH_3$)$_2$— respectively) by alkylation of the carbon atom at the α-position with respect to the carboxy group, carried out with sodium hydride and the stoichiometric amount of methyl or ethyl iodide in dimethylformamide.

Furthermore, the compounds of formula (VIII) wherein —R— is —$CH_2$— or —CH($CH_3$)— may be converted into the corresponding compounds wherein —R— represents —$CH_2$—$CH_2$— or —$CH_2$—$CH_2$—CH($CH_3$)— respectively, by the Arndt-Eisteri reaction which involves conversion of the carboxyl group CH($CH_3$)— respectively, by the Arndt-Eistert reaction which involves conversion of the carboxyl group into acyl chloride by treatment with thionyl chloride, reaction of said acyl chloride with diazomethane and conversion of the thus obtained product into the desired product by treatment with silver oxide (see F. Arndt and B. Eistert, Berichte, 68, 200 (1935)). The compounds of formula (III) wherein A represents a group —E—G wherein —E— is the group —CH($CH_3$)—CH($CH_3$)— may be prepared by treating the compound of formula G—H with an equimolar amount of an alkyl halide of formula Y—CH($CH_3$)—CH($CH_3$)—Y wherein Y is as defined above in the presence of catalytic amounts of a Lewis acid according to the Friedel-Crafts alkylation reaction and, if a compound of formula (III) is desired wherein X is different from chloro or bromo, replacing the Y group with a different leaving group.

In some particular cases, alternative processes may be employed for the preparation of compounds (III), depending on the commercial availability of the starting compounds. These alternative processes may be easily set up by any skilled technician on the basis of his chemical knowledge.

The starting compounds of formula (IV) may be prepared by reacting 4-(3-trifluoromethylphenyl)-1,2,3,6-tetrahydropyridine (II) with a compound of formula X—R—CO—G (IXa) or X—Q—CO—M (IXb) under the reaction conditions indicated above for the reaction between compounds (II) and (III).

In their turn the compounds of formula (IXa) and (IXb) may be prepared by reacting the compounds of formula H—G and H—M with an ω- haloalkanoic acid of formula Y—R—CO—Y or Y—Q—CO—Y respectively according to the methodology of the Friedel-Crafts reactions, preferably at room temperature in methylene or ethylene chloride using $AlCl_3$ as the reaction catalyst.

At the end of the reaction the desired product is isolated, for instance, by chromatography, and reacted with the compound of formula (II) to afford the compound (IV).

The compounds of formula (IXa) and (IXb) wherein —R— and —Q— are —$CH_2$— and X is chloro or bromo may also be obtained starting from the corresponding acetylated derivatives of formula $CH_3$—CO—G or $CH_3$—CO—M by treatment with an almost equimolar amount of bromine or chlorine in an inert organic solvent such as chloroform or methylene chloride.

The compounds of formula (V) may be obtained by reacting the 4-(3-trifluoromethylphenyl)-1,2,3,6-tetrahydropyridine (II) with a functional derivative of the acid of formula (VIII) G—R—CO—OH wherein —R— and —G are as defined above, in an organic solvent at a temperature comprised between −10° C. and the boiling temperature of the solvent employed.

As suitable functional derivatives, the activated free acid, the anhydride, a mixed anhydride, an active ester, or an acyl balide, preferably the chloride, may be employed. Among the active esters, the p-nitrophenyl ester is particularly preferred, but the methoxyphenyl, trytyl, benzhydryl, and the like esters may also be employed. The reaction temperature may vary between −10° C. and the boiling temperature of the solvent employed, but typically the reaction is carried out at room temperature or at a temperature of from 30° to 50° C. Preferably the reaction is carried out in the cold when it is exothermic, such as for instance when the acyl chloride is employed as the functional derivative of the acid (VIII).

As for the reaction solvents, preferred are alcohols, such as methanol or ethanol, or halogenated solvents such as methylene chloride, dichloroethane, chloroform, and the like solvents, but other organic solvents which are compatibles with the reactants employed, such as dioxane, tetrahydrofuran, and hydrocarbons, e.g. hexane, may also be employed.

The reaction may be carried out in the presence of a proton acceptor e.g. an alkali metal carbonate or a tertiary amine, when hydrochloric acid or another acid sets tree during the reaction.

Preferably, the reaction is carried out starting from the free acid in the presence of benzotriazloyl-N-oxytrisdimethylaminophosphonium hexo fluorophosphate (BOP) and of a tertiary aliphatic amine.

Finally, the compounds of formula (VI) may be prepared by cyclisation of the corresponding chlorohydrin or bromohydrin by gently heating a solution of the chloro- or bromohydrin in a polar organic solvent such as an alkanol. In its turn, the chloro- or bromohydrin may simply be obtained in situ, e.g. by reaction of the corresponding ketone with $NaBH_4$ in an alkanol such as methanol, or ethanol, and directly cyclised.

The starting compounds G-H and M-H are generally known compounds. In any case they might be prepared by the methods known in the literature for their synthesis or for the synthesis of their homologues/analogues with obvious modifications.

The new starting compounds of formula (TV) and (V) wherein —T, —R—, —G, and —M are as defined above, as well as their acid addition salts with organic or inorganic acids, represent a further specific object of the present invention.

It has been found that the compounds of formula (I), as well as their pharmaceutically acceptable acid addition salts have an intestinal prokinetic activity and may then be employed for the treatment of intestinal motility disorders and constipation.

To evaluate their anticonstipant activity, representative compounds of the present invention have been submitted to a test aimed at evaluating fecal excretion in rats.

Male rats Crl:CD(SD)BR (Charles River—Italy) weighing 220–250 g are placed at 8 a.m. in individual grid-floor contention cages. They are fasted during the test session while water is provided ad libitum. At 11:30 a.m. the test compounds are administered to the animals either orally or subcutaneously in 2 ml of water per kg of body weight. The treatment schedule is planned by means of random tables and groups of 8 animals each. At the time of drug treatment, rat rectal lumen is manually emptied from residual feces by gentle pressure and the rats are then placed again in the same cages. Fecal pellets are then collected 90 minutes after s.c. drug treatment or 210 minutes after oral treatment, their number is determined and their wet weight measured. The fecal pellets are then dried in the oven at 40° C. for 10 hours and weighed again to determine their dry weight. After 5–6 hours, the weight does not change any longer, the feces containing approximately the same percent residual humidity.

The parameter used to evaluate the activity of the test compounds is the dry weight of the feces excreted during 90 minutes (s.c.) or 210 minutes (p.o.) starting from administration of the test compound. Statistical analysis of the obtained results uses the Duncan's new multiple analysis test.

The potency of the test compounds is expressed, by means of an activity index (AI-1 g), as the dose of test compound which induces the excretion of 1 g (dry weight) of feces. Said index is extrapolated from the log dose/activity regression line ($p<0.05$). Almost no fecal excretion is observed in the concomitantly tested control animals which received the vehicle only. In the animals treated with high doses of test compounds, a maximum excretion of 12 to 16 fecal pellets with a dry weight of from about 1.4 to about 1.6 g, could be attained. With total excretions exceeding the above values, diarrhoea is clearly, observed and a correct quantification is impossible.

Representative compounds of formula (I) which may be employed for the preparation of medicaments according to the present invention showed in general an AI-1 g lower than 15 mg/kg p.o. and lower than 5 mg/kg s.c.

Particularly preferred compounds are the compounds of examples 2,6, and 7 which, tested as the corresponding hydrochlorides, showed an AI-1 g lower than 3 mg/kg p.o.

The compounds of formula (I) may be employed for the preparation of medicaments suitable for increasing intestinal motility characterised in that they contain, as the active principle, one or more compounds of formula (I) or their salts in admixture with a pharmaceutical carrier and optionally with conventional excipients.

The compounds of formula (I) as well as their pharmaceutically acceptable salts can be administered orally, rectally, sublingually, transdermally or parenterally. The oral administration route is however preferred and there is no need to utilize different administration routes. The amount of active principle which has to be administered for the treatment of intestinal motility disorders will depend, as usual, on the particular compound employed, on the nature and severity of the constipation to be treated, the weight of the patients and the administration route.

Generally, daily dosages lower than 70 mg, and preferably lower than about 40 mg are administered p.o. For parenteral administration the daily dosage will be comprised between U.1 and 25 mg.

Considering that the administration schedule has to be adapted to the patient condition, a correct practice comprises beginning the treatment with a minimal dose (from 0.1 to 5 mg, preferably from 0.5 to 2.5 mg, the lowest doses being employed for children) administered twice or three times a day and increasing then the dose or the number of administrations until the desired effects are obtained or undesired side-effects do appear.

The pharmaceutical compositions containing the compounds of formula (I) are prepared according to methods known industrial pharmacy. In particular, for the oral administration these medicaments may be in the form of tablets, capsules, elixirs or syrups.

When a solid composition is prepared in the form of tablets, the main active ingredient is mixed with a pharmaceutical carrier such as gelatin, starch, lactose, magnesium stearate, talc, arabic gum, and the like. The tablets may be coated with sucrose or other appropriate materials or they may be processed so that their dissolution rate is extended or delayed or they continuously release a predetermined amount of active principle.

A preparation in capsules may be easily obtained by mixing the active ingredient with a diluent and by filling the obtained mixture into soft or hard gelatin capsules.

A preparation in the form of syrup or elixir or to be administered as drops, may contain the active ingredient jointly with a sweetening agent, possibly acaloric, methylparaben and propylparaben as antiseptice, a flavoring agent and a suitable coloring agent, in a liquid vehicle.

Water-dispersible powders or granulates will contain the active ingredient, in admixture with dispersing or wetting agents, or with suspending agents such as polyvinylpyrrolidone and the like agents, and optionally with sweetening and/or flavouring agents.

The active principle may also be formulated in the form of microcapsules or microemulsions optionally with one or more carriers or additives.

For oral administration, each unit dosage form may advantageously contain from 0.1 to 50 mg of active principle, preferably from 0.5 to 10 mg. In certain cases, however, unit dosage forms containing a higher amount of active principle may as well be envisaged.

For parenteral administration the pharmaceutical compositions according to the present invention will contain, in addition to the active principle, one or a mixture of pharmaceutically acceptable, aqueous or non aqueous, sterile vehicles.

These pharmaceutical compositions may also contain some additives such as suitable stabilisers, wetting agents, emulsifyers, or dispersants. These compositions for parenteral administration may be sterilised e.g. by filtration through a membrane filter which removes the microorganisms (such as Millipore® filters) or by incorporation of sterilising agents to the compositions.

These compositions may also be prepared as solid formulations to be dissolved or suspended in sterile water or in another sterile injectable solvent before use.

For parenteral administration each unit dosage form may advantageously contain from 0.05 to 25 mg of active principle and preferably from 0.1 to 5 mg.

It has now been further unexpectedly been found that one of the compounds of the present invention, namely the 1-[4-(3-trifluoromethylphenyl)-1,2,3,6-tetrahydropyrid-1-yl]-2-(6,7-dimethoxynaphth-2-yl) ethane does exert neurotrophic effects on the nervous system, similar to those of NGF (Nerve Growth Factor) and increase survival of neurons.

Said effects have been demonstrated by means of an in vitro test on rat septa as follows.

SOURCE OF BIOLOGICAL MATERIAL

17–18 day old embryos were removed under flow laminary hood from gestant female Sprague Dawley rats purchased from Iffa-Credo (France).

Septa were microscopically dissected from embryonic brains in sterile conditions and dissociated with trypsin-EDTA. The resulting cell suspension was plated in a 1.1 mixture of Dulbecco Modified Eagle (DME) and Ham's F12 media (R. G. Ham, Proc. Nat. Acad. Sci., 1965, 53:288, as sold by GIBCO BRL) containing 5% fetal calf serum and 5% horse serum for 90 minutes at 37° C. This preplating contributed to the removal of non-neuronal cells.

The neuroblasts were then plated at a density of $17 \times 10^4$ cells per $cm^2$ either in a minimal serum free medium: DME/Ham's F12 (1:1) with selenium (30 nM) and transferrin (1.25 μM) or in the optimal defined $N_2$ medium described by J. E. Bottenstein, G. Sato Eds. (Cell culture in the neurosciences, 3–43, 1985) deprived or not in selenium. The wells were previously coated with poly-L-lysine and the cells were maintained at 37° C. in an incubator with a humidified 5% $CO_2$–95% air atmosphere.

Drug Treatment

Compounds to test were dissolved in dimethyl sulfoxide (DMSO) and diluted as required in culture medium. The neuroblasts were plated in wells containing the test compound or its respective solvent, and maintained for 4 days without changing the medium.

Experimental Procedure

After 4 days in culture, the medium was removed and replaced with a tetrazolium salt [3-bromo-(4,5-dimethylthiazol-2-yl)-2,5-diphenyltetrazolium] dissolved in culture medium (0.15 mg/ml). The cells were incubated for 4 hours at 37° C. The mitochondrial succinodehydrogenases of living cells reduce the tetrazolium salt to formazan blue, which after solution in DMSO is read at the optical density of 540 nm which is linearly correlated with the number of living cells (Manthorpe et al., Dev. Brain Res., 1988, 25: 191–198).

Statistical Analysis

The results were expressed as mean±SEM of the optical density obtained in the different groups (8 to 20 wells per group) The analysis of the statistical difference between the experimental and corresponding control groups was performed using the two-tailed Dunnet "t" test.

In this test, the 1-[4-(3-trifluoromethylphenyl)-1,2,3,6-tetrahydropyrid-1-yl]-2-(6,7-dimethoxynaphth-2-yl)ethane, affording survival of neuronal cells in a very poor medium, free from growth factors, this compound being more effective than those described in U.S. Pat. No. 5,270,320.

In the light of the results obtained in the above model, the use of this compound as well as of its pharmaceutically acceptable salts in the treatment and/or prevention of diseases involving neuronal degeneration can be envisaged.

A further object of the present invention is a method of treating or preventing neuronal degenerative processes which comprises administering to a mammal in need thereof the 1-[4-(3-trifluoromethylphenyl)-1,2,3,6-tetrahydropyrid-1-yl]-2-(6,7-dimethoxynaphth-2-yl)ethane or a pharmaceutically acceptable salt thereof.

More particularly the present invention concerns a method for treating or preventing memory impairments, vascular dementia, post-encephalitic disorders, post-apoplectic disorders, post-traumatic syndrome caused by brain injury, cerebral anoxic diseases, Alzheimer's disease, senile dementia, subcortical dementia such as Huntington's chorea and Parkinson's disease, AIDS dementia, neuropathies provoked by sympathetic or sensory nerve necrosis or lesions, cerebral oedema or spinocerebellar degenerations, which comprises administering to a mammal in need thereof the 1-[4-(3-trifluoromethylphenyl)-1,2,3,6-tetrahydropyrid-1-yl]-2-(6,7-dimethoxynaphth-2yl)ethane or a pharmaceutically acceptable salt thereof.

The following examples further illustrate the invention without however limiting it.

Preparation I

6,7-dimethoxy-2-naphthylacetic acid (a) A mixture of 6,7-dimethoxy-2-acetylnaphthalene (6 g, 0.026 mol), sulfur (1 g, 0.03 mol), morpholine (5.5 ml) and a catalytic amount of p-toluenensulfonic acid is heated to the reflux temperature for 4 hours. The mixture is then cooled and ethanol (20 ml) is added thereto. After standing at room temperature overnight, the precipitate is recovered by filtration and crystallised from benzene (100 ml) affording 4-[(6,7-dimethoxy-naphth-2-yl)thioacetyl]morpholine (4.8 g). M.p. 158°–161° C.

(b) A mixture of the thus obtained product (4.7 g, 0.014 mol), NaOH (2.3 g, 0.057 mol), ethanol (50 ml) and water (23 ml) is heated to the reflux temperature for 4 hours, then the mixture is concentrated to dryness and the residue is dissolved in water. The aqueous solution is washed with ethyl ether, concentrated hydrochloric acid is added thereto up to pH about 1 and the desired product is allowed to crystallise (2.3 g). M.p. 134°–136° C.

Preparation II

(6,7-dimethoxy-naphth-2-yl)oxirane (a) A solution of bromine (4.5 g, 0.029 mol) in chloroform (30 ml) is added dropwise to a solution of 6,7-dimethoxy-2-acetylnaphthalene (6.7 g, 0.029 mol) in a mixture chloroform (70 ml)/methanol (15 ml). Once the reaction mixture discoloures, it is concentrated to dryness and the residue is treated with a mixture ethyl ether/isopropyl ether. The thus obtained solid is triturated with methanol yielding 6,7-dimethoxy-2-(2-bromoacetyl)naphthalene (6 g). M.p. 120°–122° C.

(b) $NaBH_4$ (1.6 g) is added portionwise to a suspension of the above product (6 g, 0.019 mol) in methanol (80 ml). The temperature of the reaction mixture rises to 40° C. The obtained solution is stirred for 1 hour and then concentrated to dryness. The obtained residue is dissolved in ethyl acetate, the organic solution is washed with water, dried and concentrated to dryness. A residue is thus obtained which is triturated with isopropyl ether yielding the compound of the title (2.6 g). M.p. 115°–117° C.

EXAMPLE 1

1-[4-(3-trifluoromethylphenyl)-1,2,3,6-tetrahydropyrid-1-yl]-2-(6-methoxy-naphth-2-yl)propane hydrochloride (a) A solution of 6-methoxy-α-methyl-2-naphthylacetic acid (3.5 g, 0.015 mol), triethylamine (4.3 ml, 0.03 mol), 4-(3-trifluoromethylphenyl)-1,2,3,6-tetrahydropyridine hydrochloride (3.9 g, 0.015 mol), and benzotriazolyl-N-oxytris(dimethylamino)phosphonium hexafluorophosphate (BOP) (6 g, 0.015 mol) in methylene chloride (40 ml) is stirred at room temperature for 4 hours. Ethyl acetate (150 ml) is then added thereto and the mixture is washed in sequence with water, 10% NaHCO$_3$, water, 1N HCl, and water. The reaction mixture is then filtered over silica and concentrated to dryness affording 1-[4-(3-trifluoromethylphenyl)-1,2,3,6-tetrahydropyrid-1-yl]-1-oxo-2-(6-methoxy-naphth-2-yl)propane (4 g) as a thick oil.

(b) A solution of the thus obtained product in tetrahydrofuran (40 ml) is added dropwise to a suspension of LiAlH$_4$ (0.7 g, 0.018 mol) in tetrahydrofuran (10 ml) and the reaction mixture is stirred for 3 hours. Water (1.5 ml) is dropwise added thereto and stirring is prolonged for additional 2 hours. Then the mixture is filtered, the filtrate is concentrated to dryness and the thus obtained residue is dissolved in ethyl acetate (80 ml). The solution is filtered over silica and the filtrate is concentrated to dryness. The residue is dissolved in acetone and hydrogen chloride is added thereto. The hydrochloride which precipitates is recovered by filtration and crystallised from acetone (40 ml), affording 1-[4-(3-trifluoromethylphenyl)-1,2,3,6-tetrahydropyrid-1-yl]-2-(6-methoxy-naphth-2-yl)propane hydrochloride (1.5 g). M.p. 182°–184° C.

EXAMPLE 2

2-[4-(3-trifluoromethylphenyl)-1,2,3,6-tetrahydropyrid-1-yl]-1-(naphth-2-yl)ethanol hydrochloride A mixture of 4-(3-trifluoromethylphenyl)-1,2,3,6-tetrahydropyridine (2.7 g, 0.01 mol), potassium carbonate (2.7 g, 0.02 mol), and 2-naphthyl-oxirane (2.7 g, 0.015 mol) in butanol (50 ml) is heated to the reflux temperature for 2 hours. The mixture is then concentrated to dryness, the residue is dissolved in ethyl acetate, the obtained solution is washed with water, dried and concentrated to dryness. The residue is triturated with ethyl ether, filtered and dissolved in hot isopropanol. Concentrated hydrochloric acid is added thereto and the hydrochloride is allowed to crystallise, thus affording the compound of the title (1.9 g). M.p. 245°–247° C.

EXAMPLE 3

1-[4-(3-trifluoromethylphenyl)-1,2,3,6-tetrahydropyrid-1-yl]-2-(6-methoxy-naphth-2-yl)ethane hydrochloride (a) A solution of 6-methoxy-2-naphthylacetic acid (1.8 g, 0.009 mol), 4-(3-trifluoromethylphenyl)-1,2,3,6-tetrahydropyridine hydrochloride (2.4 g, 0.009 mol), triethylamine (2.4 ml, 0.018 mol), and BOP (3.7 g, 0.009 mol) in methylene chloride (40 ml) is stirred at room temperature for 5 hours. Then it is concentrated to dryness, the obtained residue is dissolved in a mixture ethyl ether/water, the organic phase is separated, and washed sequentially with 1N HCl, water, 5% NaOH, and water. The reaction mixture is then filtered over silica and the filtrate is concentrated to dryness affording 1-[4-(3-trifluoromethylphenyl)-1,2,3,6-tetrahydropyrid-1-yl]-1-oxo-2-(6-methoxy-naphth-2-yl)ethane (3.1 g). M.p. 102°–105° C.

(b) A solution of the thus obtained product (3 g, 0.007 mol) in tetrahydrofuran (30 ml) is added dropwise to a suspension of LiAlH$_4$ (0.5 g, 0.013 mol) in ethyl ether (30 ml) and the reaction mixture is stirred at room temperature for 3 hours. Water (1.2 ml) is added thereto and stirring is prolonged, still at room temperature, for additional 2 hours. Then the mixture is filtered, the filtrate is concentrated to dryness and the thus obtained residue is dissolved in ethyl acetate. The solution is washed with water and dried. Then HCl saturated isopropanol is added thereto and the hydrochloride which precipitates is recovered by filtration and crystallised from 95% ethanol (150 ml) yielding the compound indicated in the title (2 g). M.p. 260°–263° C.

EXAMPLE 4

1-[4-(3-trifluoromethylphenyl)-1,2,3,6-tetrahydropyrid-1-yl]-2-(6-hydroxy-naphth-2-yl)ethane hydrobromide A mixture of 1-[4-(3-trifluoromethylphenyl)-1,2,3,6-tetrahydropyrid-1-yl]-2-(6-methoxy-naphth-2-yl)ethane hydrochloride (0.6 g, 0.0013 mol) (obtained as described in Example 3) and 33% HBr in acetic acid (20 ml) is refluxed for 4 hours. The precipitate which forms is recovered by filtration and crystallised from 95% ethanol affording the compound indicated in the title (0.3 g) with m.p. 210°–212° C.

EXAMPLE 5

1-[4-(3-trifluoromethylphenyl)-1,2,3,6-tetrahydropyrid-1-yl]-2-(6,7-dimethyl-naphth-2-yl)ethane hydrochloride (a) A solution of 6,7-dimethyl-2-naphthylacetic acid (1 g, 0.0046 mol), 4-(3-trifluoromethylphenyl)-1,2,3,6-tetrahydropyridine hydrochloride chloride (1.2 g, 0.0046 mol), triethylamine (1.3 ml, 0.009 mol), and BOP (1.8 g, 0.0046 mol) in methylene chloride (30 ml) is stirred at room temperature for 4 hours. The mixture is then concentrated to dryness, the residue is dissolved in ethyl ether, the organic solution is washed sequentially with water, 1N NaOH, water, 1N HCl, and water. The reaction mixture is then filtered over silica and the filtrate is concentrated to dryness thus affording 1-[4-(3-trifluoromethylphenyl)-1,2,3,6-tetrahydropyrid-1-yl]-1-oxo-2-(6,7-dimethyl-naphth-2-yl)ethane (0.6 g).

(b) A suspension of the thus obtained product (0.6 g, 0.0014 mol) and LiAlH$_4$ (0.25 g, 0.006 mol) in ethyl ether (10 ml) and tetrahydrofuran (10 ml) is stirred at room temperature for 3 hours. Water (0.7 ml) is added thereto and stirring is prolonged, still at room temperature, for additional 2 hours. Then the mixture is filtered, the filtrate is concentrated to dryness and the thus obtained residue is dissolved in hot isopropanol. The solution is acidified with HCl in ethanol and allowed to crystallise thus affording the compound indicated in the title (0.2 g), M. p. 245°–247° C.

EXAMPLE 6

1-[4-(3-trifluoromethylphenyl)-1,2,3,6-tetrahydropyrid-1-yl]-2-(6,7-dimethoxy-naphth-2-yl)ethane hydrochloride (a) A mixture of 6,7-dimethoxy-2-naphthylacetic acid (2.3 g, 0.0093 mol), 4-(3-trifluoromethylphenyl)-1,2,3,6-tetrahydropyridine hydrochloride (2.4 g, 0.009 mol), triethylamine (2.5 ml, 0.018 mol), and BOP (3.8 g, 0.009 mol) in methylene chloride (50 ml) is stirred at room temperature for 4 hours. The mixture is then concentrated to dryness, the residue is dissolved in a mixture ethyl ether/water, the organic phase is separated and washed sequentially with 1N HCl, water, 1N NaOH, and water. The reaction mixture is then dried and concentrated to dryness. The obtained residue is purified by chromatography eluting with a mixture ethyl ether/ethyl acetate 1/1, thus affording 1-[4-(3-trifluoromethylphenyl)-1,2,3,6-tetrahydropyrid-1-yl]-1-oxo-2-(6,7-dimethoxy-naphth-2-yl)ethane (2.6 g).

(b) A solution of the thus obtained product (2.6 g, 0.0057 mol) in ethyl ether (40 ml) is added dropwise to a suspension of LiAlH$_4$ (0.5 g, 0.013 mol) in ethyl ether (20 ml) and the thus obtained reaction mixture is stirred at room temperature for 4 hours. Excess LiAlH$_4$ is destroyed by the cautious addition of water (1.2 ml). The reaction mixture is allowed to stand overnight and filtered. The filtrate is washed with 1N NaOH and then with water, the organic phase is dried and concentrated to dryness. The obtained residue is dissolved in isopropanol, the organic solution is made acidic by the addition of HCl and allowed to crystallise thus affording the compound of the title (1.5 g) which is recrystallised from ethanol, M.p. 215°–217° C.

EXAMPLE 7

1-[4-(3-trifluoromethylphenyl)-1,2,3,6-tetrahydropyrid-1-yl]-2-hydroxy-2-(6-dimethoxy-naphth-2-yl)ethane hydrochloride A solution of (6,7-dimethoxynaphth-2-yl)oxirane (2.5 g, 0.014 mol), 4-(3-trifluoromethylphenyl)-1,2,3,6-tetrahydropyridine (3.1 g, 0.013 mol) in ethanol (50 ml) is refluxed for 4 hours. The mixture is allowed to stand overnight and then it is filtered. The thus recovered product is dissolved in boiling ethanol (20 ml) and 37% HCl (2 ml), and allowed to crystallise therefrom thus affording the compound of the title (1.5 g). M.p. 232°–234° C.

EXAMPLE 8

1-[4-(3-trifluoromethylphenyl)-1,2,3,6-tetrahydropyrid-1-yl]-2-hydroxy-2-(pyrid-2-yl)ethane hydrochloride A mixture of 2-pyridyl-oxirane (1.21 g, 0.01 mol)(JAC3, 1976, 98(7), 1952), and 4-(3-trifluoromethylphenyl)-1,2,3,6-tetrahydropyridine (2.4 g, 0.01 mol) in absolute ethanol (45 ml) is refluxed for 4 hours. The mixture is then concentrated to dryness and the residue is purified by silica gel column chromatography eluting with a mixture ethyl acetate/methanol 9/1. The fractions which contain the desired product are pooled together, and evaporated to dryness. The residue is taken up in acetone, and hydrogen chloride saturated isopropanol is added thereto. The precipitate is recovered and crystallised from isopropanol (140 ml) thus affording the compound of the title (1.5 g). M.p. 192°–196° C.

We claim:

1. A method of treating neuronal degenerative processes which comprises administering to a mammal in need thereof, the 1-[4-(3-trifluoromethylphenyl)-1,2,3,6-tetrahydropyrid-1-yl]-2-(6,7-dimethoxy naphth-2-yl)ethane or a pharmaceutically acceptable salt thereof, wherein said compound is administered in an amount effective to treat said neuronal degeneration.

2. The method of claim 1 for the treatment of memory impairments, vascular dementia, post-encephalitic disorders, post-apoplectic disorders, post-traumatic syndrome caused by brain injury, cerebral anoxic diseases, Alzheimer's disease, senile dementia, subcortical dementia such as Huntington's chorea and Parkinson's disease, AIDS dementia, neuropathies provoked by sympathetic or sensory nerve necrosis or lesions, cerebral oedema or spinocerebellar degenerations.

3. The method of claim 2 for the treatment of vascular dementia, senile dementia and Alzheimer's disease.

* * * * *